United States Patent [19]
Van Der Brug

[11] Patent Number: 5,954,648
[45] Date of Patent: Sep. 21, 1999

[54] IMAGE GUIDED SURGERY SYSTEM

[75] Inventor: Willem P. Van Der Brug, Eindhoven, Netherlands

[73] Assignee: U.S. Philips Corporation, New York, N.Y.

[21] Appl. No.: 08/981,017

[22] PCT Filed: Apr. 29, 1996

[86] PCT No.: PCT/IB96/00384

§ 371 Date: Dec. 23, 1997

§ 102(e) Date: Dec. 23, 1997

[87] PCT Pub. No.: WO97/40763

PCT Pub. Date: Nov. 6, 1997

[51] Int. Cl.$^6$ .................................................. A61B 6/00
[52] U.S. Cl. .................... 600/411; 600/415; 600/417; 600/427; 600/429
[58] Field of Search ................................ 600/425, 411, 600/414, 415, 417, 426, 427, 429; 606/130

[56] References Cited

U.S. PATENT DOCUMENTS

| | | | |
|---|---|---|---|
| 5,165,410 | 11/1992 | Warne et al. | 600/425 |
| 5,188,110 | 2/1993 | Sugimoto | 600/425 |
| 5,299,288 | 3/1994 | Glassman et al. | 606/130 |
| 5,316,014 | 5/1994 | Livingston | 600/429 |
| 5,389,101 | 2/1995 | Heilbrun et al. | 606/130 |

*Primary Examiner*—Ruth S. Smith
*Attorney, Agent, or Firm*—Dwight H. Renfrew, Jr.

[57] ABSTRACT

An image guided surgery system comprises a position detection system which measures the position of a surgical instrument and displays the surgical instrument in its corresponding position in a CT-image or an MRI-image. The position detection system is provided with an indicator system which shows a region for which the position detection system is sensitive. Preferably, the camera unit of the position detection system incorporates a semiconductor laser which generates a light spot in the center of the operating region.

11 Claims, 1 Drawing Sheet

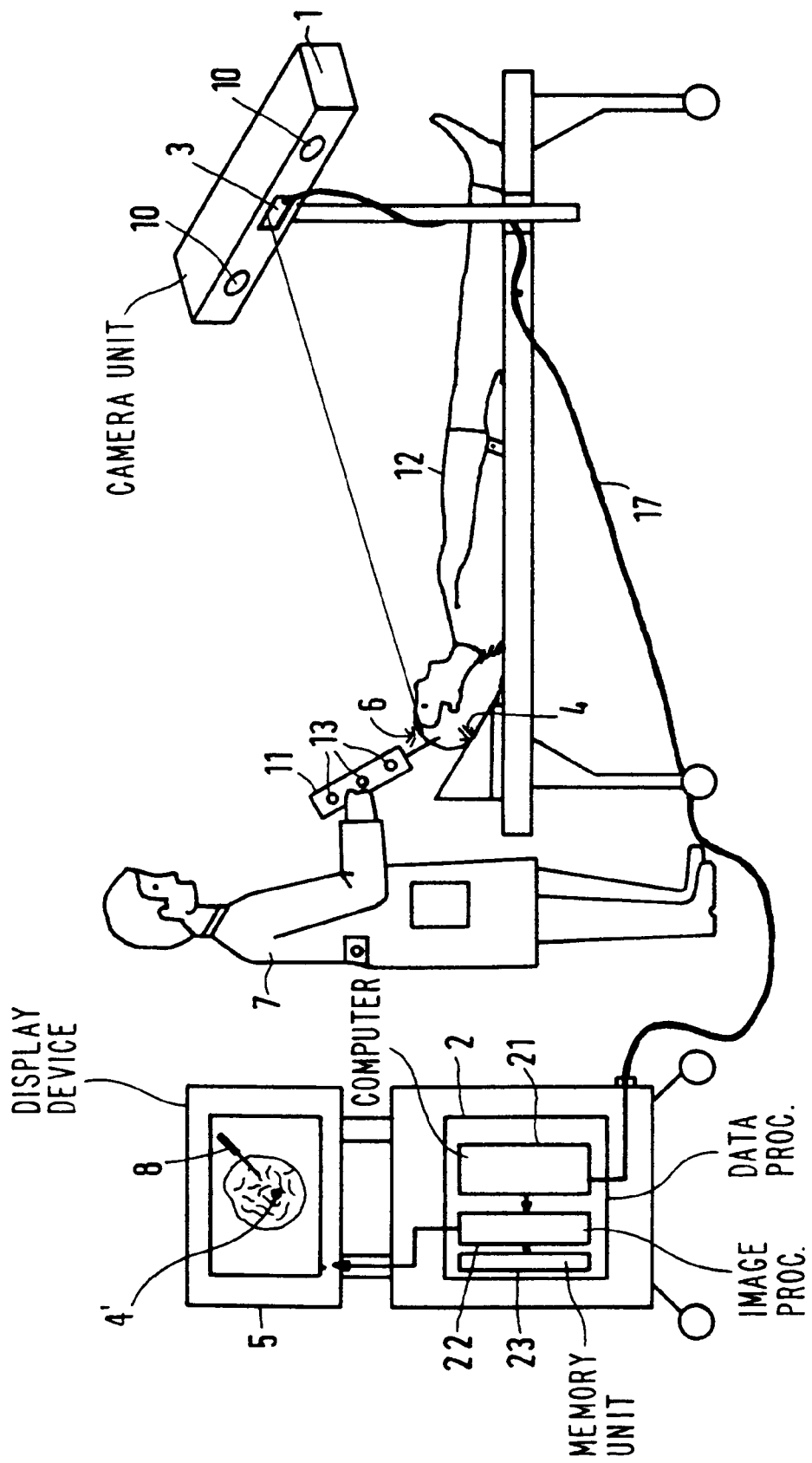

IMAGE GUIDED SURGERY SYSTEM

BACKGROUND OF THE INVENTION

1. Field of the Invention

The invention relates to an image guided surgery system comprising a position detection system.

2. Description of Related Art

Such an image guided surgery system is known from the U.S. Pat. No. 5,389,101.

Image guided surgery systems are generally employed to assist the surgeon to position a surgical instrument during an operation. During complicated surgery it is often very difficult or even impossible for the surgeon to see directly where in the interior of the patient he/she moves the surgical instrument. On a display device the image guided surgery system shows the surgeon the position of a surgical instrument relative to the region where the surgical operation is being performed. Thus, the image guided surgery system enables the surgeon to move the surgical instrument inside the patient and beyond direct sight, without risk of damaging vital parts.

The position detection system of the known image guided surgery system comprises two cameras which pick-up images of the surgical instrument from different directions. The image guided surgery system includes a data processor for deriving the position in space of the surgical instrument from image signals from both cameras. During the operation images that had been collected earlier are being shown to the surgeon. For example computed tomography (CT) image or magnetic resonance (MRI) images which were formed before the operation may be displayed on a monitor. The data processor calculates the corresponding position of the surgical instrument in the image. In the displayed image the actual position of the surgical instrument is shown together with an image of a region in which the surgical instrument is used.

Such an image guided surgery system is preferably employed in neuro-surgery to show the surgeon the position of the surgical instrument in the brain of a patient who is being operated on.

A drawback of the known image guided surgery system is that it is difficult to void that the surgical instrument is moved beyond the measuring field. Should the instrument be moved outside the measuring field, then the position detection system will no longer be able to detect the position of the surgical instrument.

SUMMARY OF THE INVENTION

An object of the invention is to provide an image guided surgery system comprising a position detection system that can be accurately directed to the operating region.

This object is achieved by an image guided surgery system according to the invention which is characterized in that the position detection system is provided with an indicator system for marking a region for which the position detection system is sensitive.

The operating region is a space in which the surgical instrument is moved during the surgical treatment. The indicator system shows, relative to the operating region, the portion of space for which the position detection system is sensitive, i.e. the measuring field of the position detection system. The measuring field is the part of space from which the camera unit picks-up images. The position detection system is directed by arranging the camera unit and the operating region relative to one another. Preferably the camera unit is directed to the operating region, but the patient to be operated on may also be moved so as to move the operating region within the measuring field of the position detection system. The indicator system shows whether or not the measuring field adequately corresponds with the operating region. The camera unit of the position detection system is easily accurately directed in that the region for which the position detection system is sensitive, i.e. such that the measuring field substantially corresponds with the operating region. Hence, complications, which would occur due to the surgical instrument leaving the measuring field are easily avoided. This reduces stress on the surgeon performing an intricate operation. Moreover, the image guided surgery system according to the invention renders unnecessary elaborate test runs for accurately directing the camera unit before the actual surgery can be started. The image guided surgery system according to the invention provides these advantages not only for surgical operations of a patient's brain or spinal cord, but also in surgery of other parts.

A preferred embodiment of an image guided surgery system according to the invention is characterized in that the indicator system is arranged to mark the center of said region.

The indicator system shows the center, that is a position substantially in the middle, of the measuring field. The position detection system is accurately directed to the operating region when the center shown by the indicator system falls substantially together with the center of the operating region. As an alternative, the indicator system is arranged to show a boundary of the measuring field. In the latter case, the position detection system is accurately directed to the operating region when the boundaries of the measuring field are shown to encompass the operation region.

A further preferred embodiment of an image guided surgery system according to the invention is characterized in that the indicator system is arranged to provide a rendition of said region on a display device.

A rendition of said region on a display device field is for example a center showing the circumference of the measuring field, or a sign indicating the center of the measuring field. The rendition of the measuring field is displayed on the display device together with the operating region. Hence, it is easy to accurately direct the position detection system such that the measuring field corresponds to the operating region. Namely, while the position detection system is being aligned, the actual measuring field is being displayed together with the operating region. Hence, the displays device shows how the measuring field is brought into correspondence with the operating region.

A further preferred embodiment of an image guided surgery system according to the invention is characterized in that the indicator system is arranged to measure an operating region.

The indicator system is arranged to detect a light source that is placed in the operating region in which the surgical instrument is going to be moved. In this embodiment preferably the camera unit of the position detection system is also employed to detect the light source as well. Instead of using a separate light source, the patient who is to be operated on may be detected. In that case, preferably an infrared camera, which may also be a camera of the position detection system, is employed. The indicator system is further arranged to display the image of the light source or the patient himself on the display device. When the measuring field does not sufficiently correspond to the operating region, then the indicator system will not be able to detect the light-source or the patient. When there is only little overlap of the measuring field with the operating region, then the light source or the patient will be detected in a peripheral region of the measuring field.

A further preferred embodiment of an image guided surgery system according to the invention is characterized in that the indicator system is arranged to generate a visible marker in said region.

The visible marker shows where the measuring field is. In particular, the visible marker shows the center of the measuring field. Thus, the location of the measuring field is indicated.

A further preferred embodiment of an image guided surgery system according to the invention is characterized in that the indicator system comprises a light source for emitting a light beam through said region, the light source being mounted on the position detection system.

The light beam falls on the operating region and generates a light spot, which forms a visible marker. Preferably, the light beam is sent through the middle of the measuring field. Then the light spot shows the center of the measuring field in the operating region. For example, when the image guided surgery system is employed in brain surgery, the position detection system is accurately directed when the light spot falls at a suitable position of the patient's head. Such suitable positions are for example the middle of the patient's head, or a position slightly above that middle. The surgeon or an assistant who chooses the position where the light spot should fall takes into account the region in which the operation is going to be performed. Moreover, it is avoided that the measuring field of the camera unit is obstructed by any equipment that is placed next to the image guided surgery system.

A further preferred embodiment of an image guided surgery system according to the invention is characterized in that the light source comprises a semiconductor laser.

A semiconductor laser emits a narrow beam of light. Moreover a semiconductor laser is cheap and has a low power consumption. Preferably, a class I semiconductor laser is employed which is harmless for the patient and staff and which emits visible light.

These and other aspects of the invention are explained in more detail with reference to the following embodiments and with reference to the drawing.

BRIEF DESCRIPTION OF THE DRAWINGS

The drawing comprises one FIGURE which shows a schematic diagram of an image guided surgery system according to the invention.

DETAILED DESCRIPTION OF THE PREFERRED EMBODIMENT

The figure shows a schematic diagram of an image guided surgery system according to the invention. The image guided surgery system comprises a position detection system which includes a camera unit 1 with one or more cameras 10 and a data processor 2. The one or several cameras pick-up images from different directions of a surgical instrument 11. For example, the camera unit 1 incorporates two CCD image sensors mounted on a rigid frame. The frame is moveable so as to direct the CCD sensors to the operating region. The image signals from separate cameras, or subsequent image signals from the single camera but from successive camera positions are supplied to the data processor 2. To that end the camera unit 10 is coupled to the data processor 2 by way of a cable 17. The data processor 2 includes a computer 21 which, on the basis of the image signals, computes the position of the surgical instrument relative to the patient 12 who is undergoing a surgical operation. The image processor 22 is incorporated in the data processor 2. The surgical instrument is fitted with light or infrared emitting diodes 13 (LEDs or IREDs) which emit radiation for which the cameras 10 are sensitive. The computer 21 also computes the corresponding position of the surgical instrument 11 in an earlier generated image such as a CT image or an MRI image. The CT data and/or MRI data are stored in a memory unit 23.

In the image data fiducial markers are imaged which are placed on particular positions on the patient. For example lead or MR-susceptible markers are placed at the ears, nose and forehead of the patient. At the start of the operation the fiducial markers are indicated with a surgical instrument filled with LEDs or IREDs and their positions in space are measured by the position detection system. The computer 21 calculates the transformation matrix which connects the positions in space of the fiducial markers to the corresponding positions of the images of the markers in the earlier generated image. This transformation matrix is subsequently used to compute a corresponding position in the image for any arbitrary position in space in the actual operating region.

The data from the memory unit 23 are supplied to the image processor 22. The position-data computed by the computer 21 are also supplied to the image processor 22. The computer 21 may be alternatively programmed to calculate the co-ordinates of the position of the surgical instrument with respect to as fixed reference system, then the image processor 22 is arranged to convert those co-ordinates to the corresponding position in the image. The image processor is further arranged to select an appropriate set of image data on the basis of the position of the surgical instrument. Such an appropriate set e.g. represents CT or MRI image data of a particular slice through the operating region. The image processor 22 generates an image signal which combines the earlier generated image data with the corresponding position of the surgical instrument. In a rendition of the earlier generated image information, also the corresponding position of the surgical instrument is displayed. Thus the surgeon 7 who handles the surgical instrument 11 can see the actual position of the surgical instrument 11 in the operating region on the display device 5. On the display device 5 e.g. a CT-image is shown with an image 8 of the surgical instrument in the corresponding positive in the CT-image. Thus the position of the surgical instrument in the operating region is shown on the display device 5. The display device is e.g. a monitor comprising a cathode-ray tube, but an LCD display screen may be used as well.

The camera unit 1 comprises an indicator system which for example includes a semiconductor laser 3. The semiconductor laser 3 is mounted on the camera unit between the cameras. The semiconductor laser emits a narrow light beam, through the measuring field of the camera unit. Preferably, that light beam is sent through the middle of the measuring field of the camera unit. At the position where the light beam falls on the operating region a light spot 6 is generated. To accurately direct the camera unit so that the measuring field of the camera unit covers the operating region the light spot 6 is positioned at the center of the operating region. In this way it is achieved that the measuring field extends in about the same amount in all directions from the center of the operating region. Hence, the risk that the surgical instrument is moved beyond the measuring field of the camera unit is small. Moreover, it is avoided that the measuring field of the camera unit is obstructed by any equipment that is placed next to the image guided surgery system. Namely, should some equipment be placed between the camera unit and the operating region, then the laser beam generates the light spot 6 on the equipment that is in the way rather than on the patient. Hence, the person directing the camera unit is immediately made aware that equipment is blocking the measuring field of the camera unit and that equipment should be re-arranged before starting surgery.

As an alternative, the indicator system includes a radiation source 4 that is positioned at the operating region. With the cameras 10 the radiation source 4 is observed. The image signals of the cameras are processed by the computer 21 and by the image processor 22. An image 4; of the radiation source is displayed on the display device 5. Preferably the image processor 22 and the monitor 5 are arranged such that the center of the measuring field of the camera unit 1 is displayed in the center of the display screen of the monitor 5. Then the camera unit 1 is accurately directed when the radiation source 4 is imaged in the middle of the display screen. Preferably, as radiation source an infrared emitting diode (IRED) is employed which emits infrared radiation for which the cameras 10 are substantially sensitive. Instead of a separate IRED, also the patient itself may be employed. In that case, the cameras 10 pick-up infrared images of the patient which are displayed on the monitor.

I claim:

1. An image guided system comprising:

a position detection system for detecting a position of a surgical instrument in an operating region of a patient to be operated on, the position detection system comprising a camera unit for picking up image signals, a memory unit for storing an image of a patient, and data processor means for processing image signals from the camera unit to detect the position of the surgical instrument and for superimposing a detected position of the surgical instrument on the stored image of the patient, and an indicator system for marking a measuring region of the operating region, the position detection system being sensitive in the measuring region, and a display for displaying the stored image of the patient with the superimposed detected position of the surgical instrument.

2. An image guided system as claimed in claim 1 wherein the indicator system comprises means for generating a visible marker in said measuring region.

3. An image guided system as claimed in claim 2 wherein the indicator system comprises a light source for emitting a light beam through said measuring region, the light source being mounted on the position detection system.

4. An image guided system as claimed in claim 3 wherein the light source comprises a semiconductor laser.

5. The image guided system of claim 2 wherein the visible marker is generated in the center of the measuring region.

6. The image guided system of claim 2 wherein the data processor means are also for superimposing a sign indicating the center of the measuring region on the stored image of the patient.

7. The image guided system of claim 2 wherein the data processor means are also for superimposing a contour indicating the circumference of the measuring region on the stored image of the patient.

8. The image guided system of claim 2 wherein the means for generating a visible marker comprises an infrared emitting diode.

9. The image guided system of claim 1 wherein the data processor means are also for superimposing a sign indicating the center of the measuring region on the stored image of the patient.

10. The image guided system of claim 1 wherein the data processor means are also for superimposing a contour indicating the circumference of the measuring region on the stored image of the patient.

11. The image guided system of claim 1 wherein the indicator system comprises means to detect a current image of the patient, and wherein the data processor means are also for superimposing the current image of the patient on the stored image of the patient.

* * * * *